United States Patent [19]

Lam

[11] Patent Number: 5,242,938

[45] Date of Patent: Sep. 7, 1993

[54] DERIVATIVES OF VIRGINIAMYCIN M1

[75] Inventor: Yiu-Kuen T. Lam, Plainsboro, N.J.

[73] Assignee: Merck & Co., Inc., Rahway, N.J.

[21] Appl. No.: 937,075

[22] Filed: Aug. 27, 1992

[51] Int. Cl.$^5$ ..................... A61K 31/42; C07D 497/08
[52] U.S. Cl. ..................... 514/375; 540/455; 540/456
[58] Field of Search .................. 540/456, 455; 514/375

[56] References Cited

U.S. PATENT DOCUMENTS

| | | | |
|---|---|---|---|
| 4,762,923 | 8/1988 | Lam et al. | 540/455 |
| 4,772,595 | 9/1988 | Lam et al. | 514/183 |
| 4,859,690 | 8/1989 | Lam et al. | 514/375 |
| 4,894,370 | 1/1990 | Lam et al. | 514/183 |
| 4,942,230 | 7/1990 | Lam et al. | 540/456 |
| 5,006,466 | 4/1991 | Lam et al. | 435/120 |

FOREIGN PATENT DOCUMENTS

| | | | |
|---|---|---|---|
| 0135410 | 3/1985 | European Pat. Off. | 514/375 |
| 0248703 | 12/1987 | European Pat. Off. | 514/375 |
| 0252720 | 1/1988 | European Pat. Off. | 514/375 |

OTHER PUBLICATIONS

Anteunis, et al., *Bull. Soc. Chim. Belg.*, 97(3), 209-217 (1988).
Le Goffic, *J. Antimicrob. Chemo.*, 16 Supp. A, 13-21 (1985).
De Meester, et al., *J. Antibiotics*, 29(12), 1297-1305 (1976).
Lam, et al., *J. Antibiotics*, 44(6), 613-625 (1991).

*Primary Examiner*—Robert T. Bond
*Attorney, Agent, or Firm*—J. Eric Thies; Richard C. Billups

[57] ABSTRACT

Dicarbonyloxy, carbonyloxy, carbanilate, and dihydroxy derivatives of Virginiamycin $M_1$ are useful antibiotics and effectively bind gastrin and brain CCK receptors.

15 Claims, No Drawings

DERIVATIVES OF VIRGINIAMYCIN M1

BACKGROUND OF THE INVENTION

The present invention relates to Virginiamycin $M_1$ derivatives. More particularly, the present invention relates to Virginiamycin $M_1$ derivatives characterized by a carbonyloxy or a hydroxy substituent at the 13-position and 15-position of the macrolide, or a carbonyloxy or a carbanilate substituent at the 13-position of the macrolide.

Cholecystokinin (CCK) and gastrin (G) are regulatory peptides which are found in gastrointestinal tissue and in the central nervous system, Mutt, Gastrointestinal Hormones, Glass, Ed. Raven Press, N.Y., p: 169 (1980). The CCK peptides reportedly co-exist with dopamine in certain mid-brain neurons and thus may play a role in the functioning of dopaminergic systems in the brain, as well as serving as neurotransmitters, Prange et al., Ann. Repts. Med. Chem. 17:31 (1982). Gastrointestinal CCK and gastrin may act on parietal and chief cells of the fundic glands of the mammalian gastric mucosa to stimulate acid and pepsinogen secretion, Chew and Hersey, Am. J. Physiol. 242:G504 (1982). Cholecystokinins are also believed to be physiological satiety hormones and, thus, may play a role in appetite regulation, Smith, Eating and Its Disorders, Stunkard and Steller, Eds., Raven Press, N.Y., p. 67 (1984). Additional effects of CCKs include the stimulation of colonic motility, gall bladder concentration, pancreatic enzyme secretion and the inhibition of gastric emptying.

Intestinal CCK exists in 39- and 33-amino acid forms with the C-terminal 33-amino acid residues being identical. Biological activity is restricted to the C-terminal heptapeptide of the native peptide and a C-terminal octapeptide has the same efficacy as CCK-33 but is approximately ten-times more potent, Jensen et al., Proc. Natl. Acad. Sci. USA 77:2079 (1980).

Gastrin also occurs naturally in several different forms; 34-amino acids, 17-amino acids and 13-amino acids with the tyrosine being either sulfated or unsulfated. The 17- and 13-amino acid forms can be viewed as C-terminal fragments of the 34-amino acid form. The different forms exhibit varying potency for stimulating gastric acid secretion. Gastrin-17 is 5 times more potent than Gastrin-34 and 2.5 times more potent than Gastrin-13, Walsh and Grossman, New Engl. J. Med. 292:1324,1377 (1975). gastrin and CCK share a common C-terminal pentapeptide amide sequence, Gly-Trp-Met-Asp-Phe-$NH_2$.

Gastrin and CCK antagonists of the Virginiamycin family are useful for treating diseases mediated by gastrin and CCK. CCK antagonists are successful in preventing or treating CCK-related disorders of the gastrointestinal, central nervous and appetite regulatory systems of animals, especially of humans. Antagonists of CCK are also useful in potentiating and prolonging opiate-mediated analgesia and thus have utility in the treatment of pain, Faris et al., Science 226:1215 (1984). Gastrin antagonists are useful in the treatment and prevention of gastrin-related disorders of the gastrointestinal system in humans and animals, such as ulcers, Zollinger-Ellison syndrome, antral G cell hyperplasia and other conditions, in which reduced gastrin activity is of therapeutic value. CCK and gastrin also have tropic effects on certain tumors, Ohyama, Hokkaido J. Med. Sci., 60, 206 (1985), and antagonists of CCK and gastrin are useful in treating these tumors.

Antibiotics of the Virginiamycin family have been used as food additives to improve the growth of poultry, swine and cattle. Although growth promotion by antibiotics is not thoroughly understood, there is little doubt that the effect is due in part to an inhibition of the intestinal flora, Coccito, Micro. Rev. 43:145 (1979). Virginiamycin $M_1$ and related antibiotics are generally specific for gram-positive bacteria and prevent cell multiplication. The virginiamycin antibiotics are most effective when in their complex form, that is when they are composed of both M and S components, Coccito. Micro. Rev. 43:145 (1979). The wide use of these antibiotics as growth promoters relates to their low toxicity, lack of accumulation in animal tissues, no production of resistant mutants and a rapid degradation in animal feces.

Virginiamycin $M_1$ and certain derivatives have been previously reported (J. Antibiotics, 44, 613–625 (1991)).

DETAILED DESCRIPTION OF THE INVENTION

The present invention provides a novel I Virginiamycin $M_1$ derivative of the formula I:

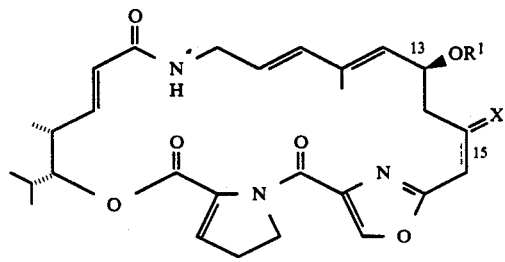

or a pharmaceutically acceptable salt thereof, wherein:
$R^1$ is selected from the group consisting of:
 (1) hydrogen
 (2) —$COR^2$, wherein $R^2$ is selected from the group consisting of:
  (a) $C_{1-4}$ alkyl,
  (b) benzyl, and
  (c) phenyl,
 (3) —$CONHR^3$, wherein $R^3$ is selected from the group consisting of:
  (a) $C_{1-4}$ alkyl,
  (b) benzyl, unsubstituted or substituted with —$CH_3$ or —$NO_2$,
  (c) phenyl, unsubstituted or substituted with —$CH_3$ or —$NO_2$,
  (d) naphthyl, unsubstituted or substituted with —$CH_3$ or —$NO_2$,
X is oxo, (H, OH) or (H, —$OCOR^4$), wherein $R^4$ is independently selected from the definitions of $R^2$,
and the symbol of a line and a dashed line is a single bond or a double bond; with the proviso that if X is oxo or (H, OH), the symbol of a line and a dashed line is a single bond; and the further proviso that if X is oxo, $R^1$ is other than hydrogen.

In particular, the present invention provides novel Virginiamycin $M_1$ derivatives of the formula II:

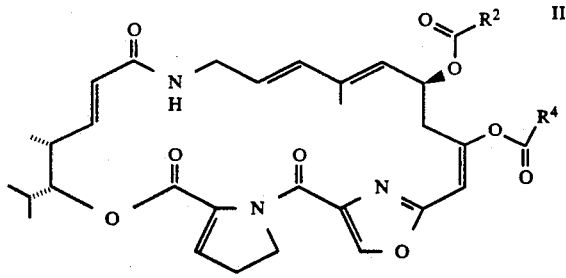

wherein $R^2$ and $R^4$ are independently selected from the group consisting of $C_{1-4}$alkyl, benzyl or phenyl.

The present invention also provides novel Virginiamycin $M_1$ derivatives of the formula III:

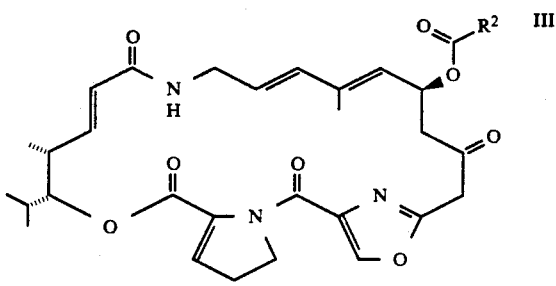

wherein $R^2$ is independently selected from the group consisting of $C_{1-4}$alkyl, benzyl or phenyl;

The present invention also provides novel Virginiamycin $M_1$ derivatives of the formula IV:

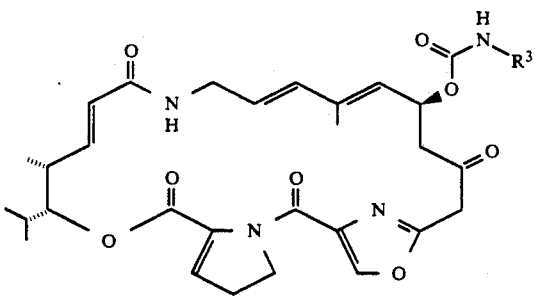

wherein $R^3$ is selected from the group consisting of $C_{1-4}$alkyl, phenyl, benzyl or naphthyl, each optionally mono-substituted with methyl or $-NO_2$;

The present invention further provides Virginiamycin $M_1$ derivatives of the formula V:

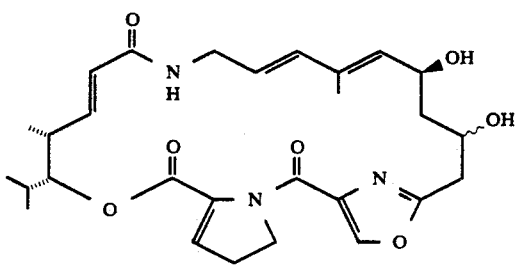

The present invention also provides novel methods for treating gastrointestinal disorders, central nervous system disorders, regulating appetite in mammals and treating bacterial infections.

The manufacture of compounds of the present invention is essentially a two-step process. Firstly, Virginiamycin $M_1$ is produced by art known methods and, secondly, this compound is derivatized to produce the compounds herein.

Virginiamycin $M_1$ is a known natural product produced by fermentation of a species of Streptomyces. A sample of a particular effective species of Streptomyces has been deposited in the American Type Culture Collection, 12301 Parklawn Drive, Rockville, Md. 20852, USA, on Jul. 29, 1986, under the "Budapest Treaty on the International Recognition of the Deposit of Microorganisms for the Purposes of Patent Procedure" and has been assigned ATCC number 53527.

The Streptomyces species was isolated from soil associated with three roots in Pimpri, India and expresses morphological and cultural characteristics as shown in the following table:

TABLE I

| | |
|---|---|
| Morophology: | Sporophores form very loose coils, chains are more than 15 spores in length, spores are spherical to oval, and are about 0.9μ to 0.9 × 1.2μ in size. |
| Cultural Char.: | Yeast extract malt extract agar (ISP Medium 2) |
| V: | Reverse - grayish brown edged with gray |
| A: | Light gray mixed with white and edged with dark gray. |
| SP: | None |
| | Oatmeal agar (ISP Medium 3) |
| V: | Reverse - light grayish tan edged with gray |
| A: | Light gray mixed with white, edged with dark gray |
| SP: | None |
| | Inorganic salts starch agar (ISP Medium 4) |
| V: | Reverse - grayish tan edged with gray |
| A: | Light gray mixed with white, edged with dark gray |
| SP: | None |
| | Glycerol asparagine agar (ISP Medium 5) |
| V: | Reverse - tan edged with gray |
| A: | Light gray and white edged with light gray |
| SP: | None |
| | Peptone iron-yeast extract agar (ISP Medium 6) |
| V: | Reverse - tan |
| A: | Pale gray mixed with white and edged with medium gray |
| SP: | None |
| Melanin: | None |
| | Tyrosine Agar (ISP Medium 7) |
| V: | Reverse - tan edged with brown |
| A: | Mixed grayish - white and gray edged with dark gray |
| SP: | Slight browning of medium |
| | Czapek-Dox Agar |
| V: | Reverse - grayish tan |
| A: | Light gray mixed with white |
| SP: | Slight browning of medium |

V = vegetative growth: A = aerial mycelium: SP = soluble pigment

Color number designations taken from Color Harmony Manual, 1958, 4th Edition, Container Corporation of America, Chicago, Ill.

The carbon utilization of ATCC 53527 was determined using Pridham-Gottlieb basal medium (ISP Medium 9) supplemental with 1% carbon sources as seen in the following table:

TABLE II

| | | | |
|---|---|---|---|
| Glucose | + | Mannitol | + |
| Arabinose | + | Mannose | + |
| Cellulose | − | Raffinose | ± |
| Fructose | + | Rhamnose | + |
| Inositol | + | Sucrose | + |
| Lactose | + | Xylose | + |
| Maltose | + | | |

[+ = growth: ± growth poor or questionable: − = no growth as compared to negative control (no carbon source)].

The temperature growth range and oxygen requirements were determined using yeast extract-dextrose +− salts agar. The results are shown in the following table:

TABLE III

Temperature range (Yeast extract-dextrose + salts agar)

| | |
|---|---|
| 28° C.− | Good vegetative growth and sporulation |
| 37° C.− | Good vegetative growth and sporulation |
| 42° C.− | No growth |
| 50° C.− | No growth |
| Oxygen requirements (Stab culture in yeast extract-dextrose + salts agar) | Aerobic |

All readings taken after three weeks at 28° C. unless noted otherwise. pH of all media approximately neutral (6.8–7.2).

The cultural characteristics of this organism are compared with culture descriptions of Streptomyces species described in Berger's Manual of Determinative Bacteriology, Eighth Edition, 1974, Williams & Wilkens, Baltimore, Md., and the Streptomeyces species is presumptively identified as a strain of Streptomyces olivaceus.

The fermentation is carried out at a temperature range of from about 20° C. to about 37° C., with 28° C. being preferred. Generally, the composition of the assimilable nutrient medium may be varied over a wide range. The essential nutrient ingredients are a carbon source and a nitrogen source. Other essential nutrients are provided via mineral salts such as chlorides, nitrates, sulfates, carbonates and phosphates of sodium, potassium, ammonium and calcium. The nutrient medium may also contain sources of inorganic trace elements such as magnesium, iron, copper, manganese, zinc, cobalt and the like.

Typical sources of carbon include; sugars, oils, organic acids, dextrin, starches, glycerol and the like. Typical nitrogen sources include; amino acids, vegetable meals, and extracts (e.g., malts, soy, cotton seed, figs, tomato, corn, etc.), animal viscera, various hydrolysates (e.g., casein, yeast, etc.) and industrial by-products such as lard water and distillers solubles.

The maximum yield of virginiamycin $M_1$ is achieved within about 24 to about 96 hours, usually in about 48 to about 72 hours, of fermentation under optimum conditions. The inoculum for the fermentation is provided from vegetative growth in a medium which supports rapid growth of the microorganism or by direct inoculation of frozen biomass.

The terms "seed" and "production" media are employed as terms of art. Generally, a seed medium supports rapid growth of the microorganism and an aliquot (seed) of this medium is used to inoculate a production medium for a large scale fermentation.

Following fermentation, the accumulated virginiamycin $M_1$ is recovered from the culture broth by conventional chromatographic means. The isolated compound is separated by reverse phase high performance chromatography.

Virginiamycin $M_1$ is isolated from whole fermentation broth by the addition of a nearly equal volume of a moderately polar solvent immiscible in water. Such solvents include chloroform, ethyl acetate, methyl ethyl ketone and the like, with methyl ethyl ketone being preferred. The layers are allowed to settle and the organic layer collected. The organic layer contains virginiamycin $M_1$.

The active organic layer isolated from the culture broth is flash evaporated under reduced pressure at a temperature of about 30° C. to about 50° C., with 40° C. being preferred, and partitioned between a saturated hydrocarbon such as hexane and an alcohol such as methanol. The methanol layer is flash evaporated at about 30° C. to about 50° C., with 40° C. being preferred, under pressure and chromatographed on silica gel using a mobile phase of acetone about 50% to about 75% in hexane. The active fraction is purified by reverse phase high performance liquid chromatography (HPLC).

Derivatization of the Virginiamycin $M_1$ may be conducted according to Scheme A. As shown in Scheme A, Virginiamycin $M_1$, is reacted with an anhydride in the presence of pyridine in an aprotic solvent at room temperature to produce dicarbonyloxy derivatives of the instant invention.

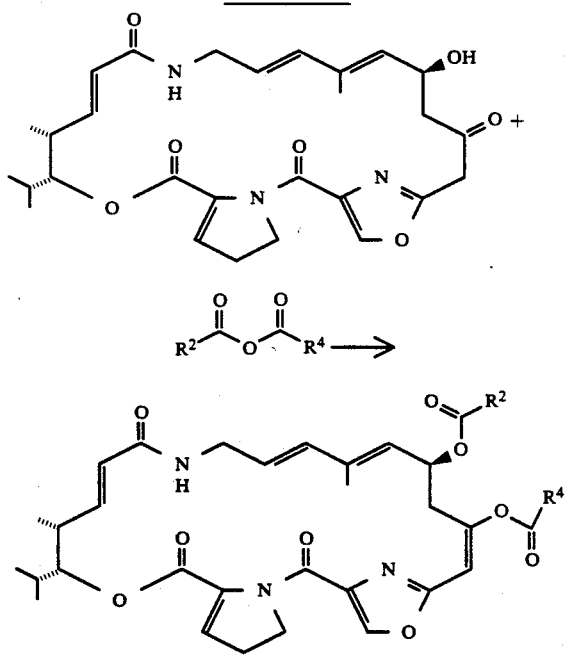

SCHEME A

Preferred $R^2$ and $R^4$ groups are methyl, ethyl, propyl, i-propyl, n-butyl, i-butyl, n-butyl, hexyl, benzyl and phenyl. Thus preferred anhydrides include acetic anhydride, propionic anhydride, i-propionic anhydride, butyric anhydride, i-butyric anhydride, hexanoic anhydride and the corresponding mixed anhydrides.

Similarly, as shown in Scheme B Virginiamycin $M_1$ compound may be reacted with an anhydride in the presence of pyridine in an aprotic solvent at room temperature to produce carbonyloxy derivatives of the instant invention.

SCHEME B

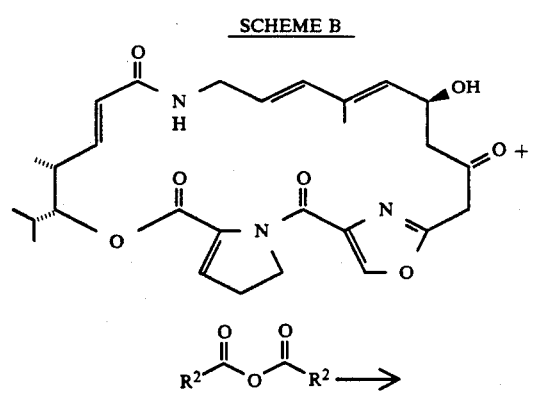

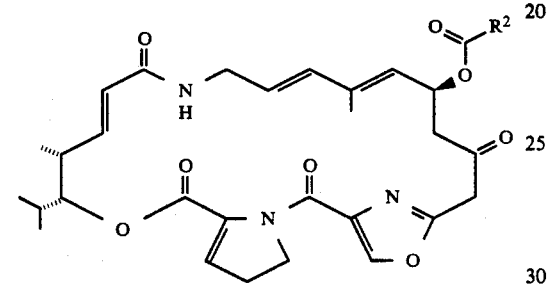

In another reaction, derivatization of Virginiamycin $M_1$ proceeds generally according to Scheme C. Virginiamycin $M_1$ may be reacted with the appropriate acid chloride in an aprotic solvent at room temperature to produce carbonyloxy derivatives of the instant invention.

SCHEME C

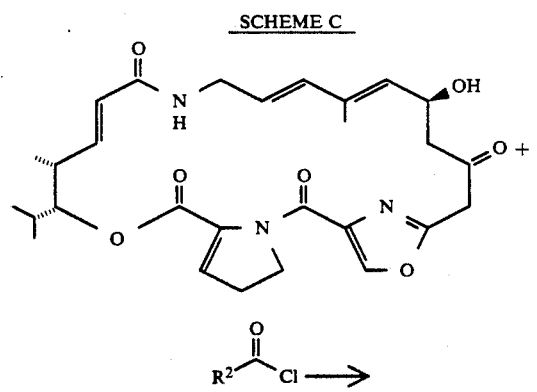

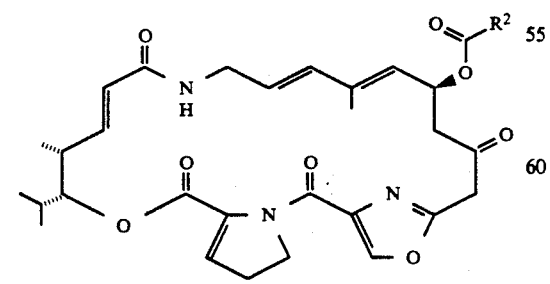

Preferred $R^2$ groups are methyl, ethyl, propyl, i-propyl, n-butyl, i-butyl, n-butyl, hexyl, benzyl and phenyl. Thus preferred acid halides include acetyl chloride, propionyl chloride, butyryl chloride, hexanoyl chloride, benzoyl chloride and phenylacetyl chloride.

In addition, as shown in Scheme D, Virginiamycin $M_1$ may be reacted with an isocyante in the presence of pyridine and/or 4-dimethylaminopyridine in an aprotic solvent at or above room temperature to produce carbanilate derivatives of the instant invention.

SCHEME D

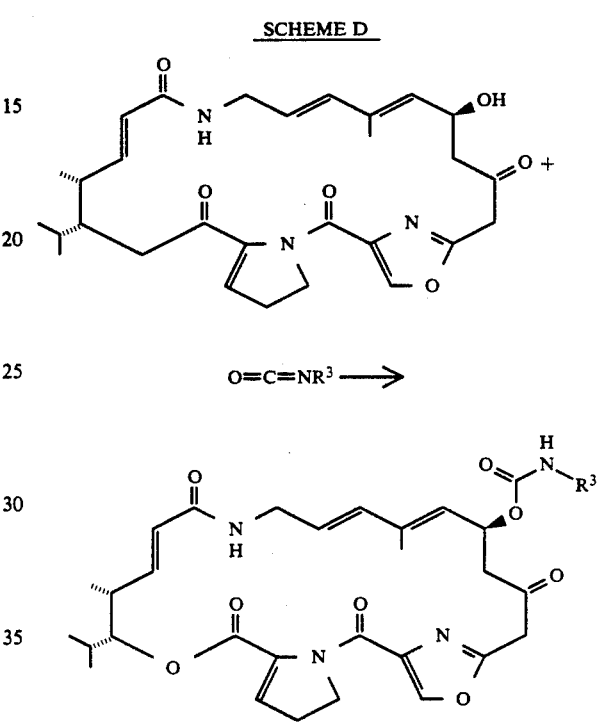

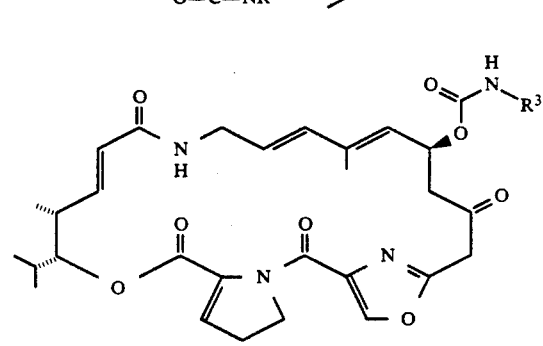

Preferred $R^3$ are methyl, ethyl, propyl, i-propyl, n-butyl, i-butyl, n-butyl, benzyl, phenyl, o-nitrophenyl, m-nitrophenyl, p-nitrophenyl, o-tolyl, m-tolyl, p-tolyl, naphth-1-yl or naphth-2-yl.

Also, as shown in Scheme E, Virginiamycin $M_1$ may be reacted with sodium borohydride in an appropriate organic solvent such as methanol at or below room temperature to produce dihydroxy compounds of the instant invention.

SCHEME E

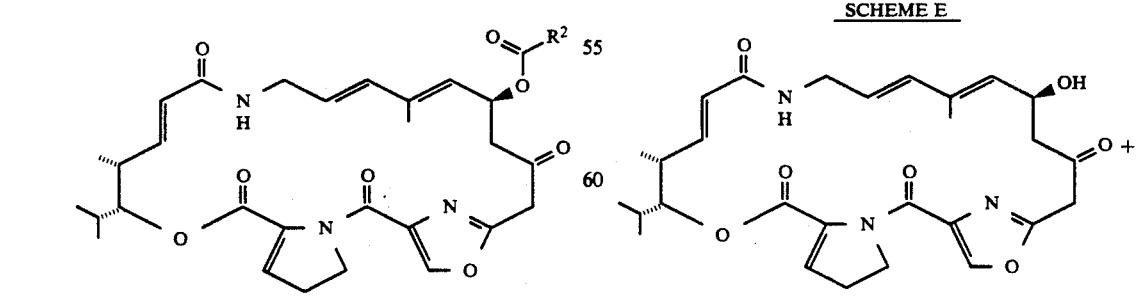

-continued
SCHEME E

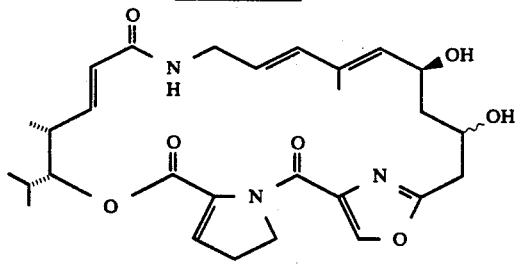

Virginiamycin $M_1$ and the compounds herein bind to both CCK and gastrin receptors. Thus, virginiamycin $M_1$ and the compounds herein may have a unique function in appetite regulation, the treatment of CCK-related disorders of the gastrointestinal and central nervous system. The action of the instant compounds as gastrin antagonists will allow their use in the treatment and prevention of gastrin-related disorders such as ulcers, Zollinger-Ellison syndrome and antral G cell hyperplasia. The compounds also function as antibiotic agents and can be used to treat microbial infections.

The compounds herein can be administered to mammals, including humans, either alone, or preferably, in combination with pharmaceutically acceptable carriers or diluents, in a pharmaceutical composition, according to standard pharmaceutical practice. The compounds can be administered orally or parenterally. Parenteral administration includes intravenous, intramuscular, intraperitoneal, subcutaneous, and topical administration.

For oral use as CCK or gastrin antagonists or as antibiotics, the selected compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. For oral use as antibiotics in domestic animals, the compounds are added to the animal feed. If desired, certain sweetening and/or flavoring agents can be added. For intramuscular, intraperitoneal, subcutaneous, and intravenous use, sterile solutions of the active ingredient are usually prepared, and the pH of the solutions should be suitably adjusted and buffered. For intravenous use, the total concentration of solutes should be controlled to render the preparation isotonic.

When the compounds are used as a CCK or gastrin antagonist or an antibiotic in a human subject, the daily dosage will normally be determined by the prescribing physician. Moreover, the dosage will vary according to the age, weight, and response of the individual patient, as well as the severity of the patient's symptoms. However, in most instances, an effective daily dosage will be in range from about 1 mg to about 1500 mg and preferably 10 mg to 500 mg in a single or divided doses. On the other hand, it may be necessary to use dosages outside these limits in some cases.

When the compounds are used as an oral antibiotics for domestic animals, the daily dosage will be determined according to the age, weight, and species of animal being treated. The effective dosage will be in the range from about 5 to about 200 parts per million per volume of food.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

EXAMPLE 1

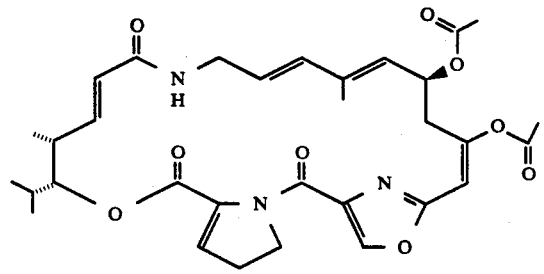

Acetic anhydride (45 ml) was added to a stirring solution of Virginiamycin $M_1$ (6.5 g) in anhydrous pyridine (45 ml) at room temperature. After 30 minutes, ice-cold methanol (85 ml) was added in portions. Stirring was continued for 20 more minutes followed by flash evaporation to dryness at room temperature. The residue was partitioned between dichloromethane ($3 \times 300$ ml) and saturated NaCl (aq, 300 ml). The organic layers were pooled, dried over anhydrous $Na_2SO_4$, flash evaporated to dryness (dry weight=8.1 g) and purified over E. Merck silica gel 60 column in hexane/acetone mixtures to give 1.0 g of the monoacetate and 1.58 g of the diacetate.

HREI-MS($M^+$): calculated for $C_{32}H_{39}N_3O_9$: 609.2686; found: 609.2674

300 MHz $H^1$-NMR($CD_2Cl_2$), $\delta$(ppm): 5.66(m), 2.00 (3H, s, $CH_3$), 2.20 (3H, s, $CH_3$), 6.23 (1H, s, H-16)

75 MHz $C^{13}$-NMR($CD_2Cl_2$), $\delta$(ppm): 11.9, 13.3, 19.0, 19.8, 21.3, 29.8, 30.4, 36.5, 38.6, 40.8, 50.6, 69.6, 82.8, 108.5, 122.1, 125.5, 127.0, 128.5, 128.6, 129.3, 133.6, 135.6, 137.2, 142.6, 143.8, 155.8, 158.4, 161.1, 161.8, 167.3, 169.0, 170.1

FT-IR(ZnSe), $\nu$(cm$^{-1}$): 3362, 2973, 1766, 1736, 1671, 1621

UV(MeOH), $\lambda_{max}$(nm, E %): 213 (sh, 437), 237 (552), 280 (sh, 217)

$R_f$=0.22 (E. Merck silica gel 60 F TLC plates (0.2 mm), $Me_2CO$:hexane, 40:60)

EXAMPLE 2

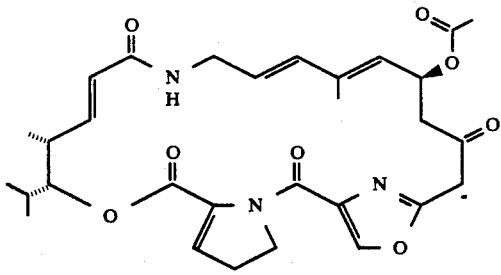

Acetic anhydride (45 ml) was added to a stirring solution of Virginiamycin $M_1$ (6.5 g) in anhydrous pyridine (45 ml) at room temperature. After 30 minutes, ice-cold methanol (85 ml) was added in portions. Stirring was continued for 20 more minutes followed by flash evaporation to dryness at room temperature. The residue was partitioned between dichloromethane (3×300 ml) and saturated NaCl (aq, 300 ml). The organic layers were pooled, dried over anhydrous $Na_2SO_4$, flash evaporated to dryness (dry weight=8.1 g) and purified over E. Merck silica gel 60 column in hexane/acetone mixtures to give 1.0 g of the monoacetate and 1.58 g of the diacetate.

HR FAB-MS(M+H+): calculated for $C_{30}H_{37}N_3O_8+H$: 568.2658; found: 568.2639

(300 MHz)$H^1$-NMR($CD_2Cl_2$), δ(ppm): 5.76(m), 1.95 (3H, s, $CH_3$)

(300 MHz)$C^{13}$-NMR($CD_2Cl_2$), δ(ppm): 12.4, 12.9, 18.9, 19.7, 21.2, 30.2, 30.6, 38.1, 40.2, 45.1, 46.0, 51.1, 68.2, 81.7, 123.7, 125.6, 126.6, 127.5, 132.9, 136.3, 136.9, 137.2, 143.4, 145.7, 156.3, 160.8, 161.1, 167.2, 170.0, 199.3

FT-IR(ZnSe), ν(cm$^{-1}$): 3356, 2971, 1733, 1673, 1621
UV(MeOH), $\lambda_{max}$(nm, E %): 226 (495), 280 (sh, 149)
$R_f$=0.31 (E. Merck silica gel 60 F TLC plates (0.2 mm), $Me_2CO$: hexane, 40:60)

EXAMPLES 3-6

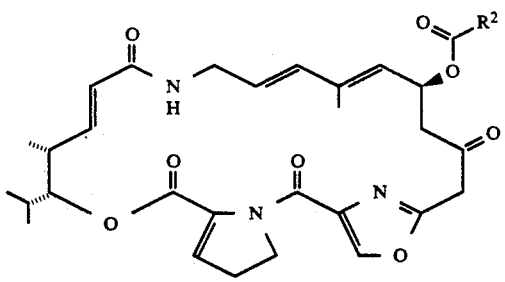

$R^2$ = —$CH_2CH_3$
= n-butyl
= —$CH_2C_6H_5$
= —$C_6H_5$

The n-propionate, n-valerate, n-phenylacetate and benzoate derivatives of Virginiamycin $M_1$ were prepared using the respective carbonyl chlorides. The respective carbonyl chloride (1.0 mmole) was added to a stirring solution of virginiamycin $M_1$ (0.50 g, 0.95 mmole), pyridine (84 μl) and 4-dimethylaminopyridine (20 μg) at room temperature for 2 hours. Methanol (0.5 ml) was added to destroy excess reagent. The reaction mixture was partitioned between dichloromethane (3×5 ml) and saturated NaCl (aq) (50 ml). The pooled organic layers were dried over anhydrous $Na_2SO_4$ and flash evaporated to dryness (dry weight=0.63, 0.81, 1.0 and 1.4 g respectively). Purification over a column of 50 g E. Merck silica gel 60 (43-60 μm particle size) in 40-80% acetone/hexane stepwise gradients yielded 0.43, 0.33, 0.29 and 0.56 g of the respective esters.

$R^2$=$CH_2CH_3$ (Compound 3)
HREI-MS(M+): calculated for $C_{31}H_{39}N_3O_8$: 581.2737; found: 581.2737

(300 MHz)$H^1$-NMR($CD_2Cl_2$), δ(ppm): 5.77(m), 1.05 (3H, t, J=7.5, $CH_2CH_3$), 2.23 (2H, q, J=7.5, $CH_2CH_3$)

(300 MHz)$C^{13}$-NMR($CD_2Cl_2$), δ(ppm): 9.1, 12.4, 12.9, 18.9, 19.7, 27.8, 30.2, 30.5, 38.1, 40.3, 45.2, 45.9, 51.1, 68.0, 81.6, 123.7, 125.5, 126.7, 127.3, 132.9, 136.3, 136.8, 137.1, 143.5, 145.7, 156.3, 160.8, 161.1, 167.2, 173.4, 199.4

FT-IR(ZnSe), ν(cm$^{-1}$): 3345, 2973, 1733, 1673, 1621
UV(MeOH), $\lambda_{max}$(nm, E %): 226 (476), 280 (134)
$R_f$=0.25 (E. Merck silica gel 60F TLC plates (0.2 mm), $Me_2CO$:hexane, 40:60)

$R^2$=—$CH_2CH_2CH_2CH_3$ (Compound 4)
HREI-MS(M+): calculated for $C_{33}H_{43}N_3O_8$: 609.3050; found: 609.3061

(300 MHz)$H^1$-NMR($CD_2Cl_2$), δ(ppm): 5.78(m), 0.88 (3H, t, J=7.5, $CH_2CH_2CH_2CH_3$), 1.30 (2H, m, $CH_2CH_2CH_2CH_3$), 1.53 (2H, m, $CH_2CH_2CH_2CH_3$), 2.22 (2H, t, J=7.5, $CH_2CH_2CH_2CH_3$), (300 MHz)$C^{13}$-NMR($CD_2Cl_2$), δ(ppm): 12.4, 12.9, 13.8, 18.9, 19.7, 22.5, 27.2, 30.2, 30.5, 34.3, 38.1, 40.3, 45.2, 45.9, 51.1, 68.0, 81.6, 123.7, 125.5, 126.7, 127.3, 133.0, 136.3, 136.8, 137.2, 143.6, 145.7, 156.3, 160.8, 161.2, 167.3, 172.7, 199.4

FT-IR(ZnSe), ν(cm$^{-1}$): 3355, 2966, 1733, 1673, 1621
UV(MeOH), $\lambda_{max}$(nm, E %): 210 (sh, 450), 226 (489), 280 (sh, 132)
$R_f$=0.36 (E. Merck silica gel 60F TLC plates (0.2 mm), $Me_2CO$:hexane, 40:60)

$R^3$=—$CH_2C_6H_5$ (Compound 5)
HREI-MS(M+): calculated for $C_{36}H_{41}N_3O_8$: 643.2893; found: 643.2894

(300 MHz)$H^1$-NMR($CD_2Cl_2$), δ(ppm): 5.80(m), 3.65 (2H, s, $CH_2C_6H_5$), 7.50 (5H, m, $C_6H_5$)

(300 MHz)$C^{13}$-NMR($CD_2Cl_2$), δ(ppm): 12.4, 12.9, 18.9, 19.7, 30.2, 30.5, 38.1, 40.4, 41.4, 45.2, 45.9, 51.1, 68.7, 81.6, 123.8, 125.4, 126.3, 127.3, 127.4, 128.8, 128.8, 129.6, 129.6, 129.7, 132.9, 136.3, 137.13, 137.17, 143.7, 145.6, 156.3, 160.8, 161.1, 167.5, 170.7, 199.2

FT-IR(ZnSe), ν(cm$^{-1}$): 3356, 2972, 1733, 1673, 1621
UV(MeOH), $\lambda_{max}$(nm, E %): 213 (476), 230 (sh, 445), 280 (sh, 110)
$R_f$=0.28 (E. Merck silica gel 60F TLC plates (0.2 mm), $Me_2CO$:hexane, 40:60)

$R^2$=—$C_6H_5$ (Compound 6)
HR FAB—MS(M+): calculated for $C_{35}H_{39}N_3O_8$: 629.2737; found: 629.2702

(300 MHz)$H^1$-NMR($CD_2Cl_2$), δ(ppm): 6.03(m), 7.36-7.61 (5H, m, $C_6H_5$)

(300 MHz)$C^{13}$-NMR($CD_2Cl_2$), δ(ppm): 12.4, 13.0, 18.9, 19.7, 30.2, 30.6, 38.1, 40.3, 45.3, 46.0, 51.1, 68.9, 81.6, 123.7, 125.5, 126.4, 127.6, 128.7, 128.7, 129.8, 129.8, 130.5, 132.9, 133.3, 136.3, 137.15, 137.25, 143.5, 145.7, 156.3, 160.9, 161.1, 165.6, 167.3, 199.3

FT-IR(ZnSe), ν(cm$^{-1}$): 3357, 2971, 1727, 1673, 1621
UV(MeOH), $\lambda_{max}$(nm, E %): 208 (sh, 447), 232 (607), 280 (sh, 145)

$R_f=0.21$ (E. Merck silica gel 60F TLC plates (0.2 mm), Me$_2$CO:hexane, 40:60)

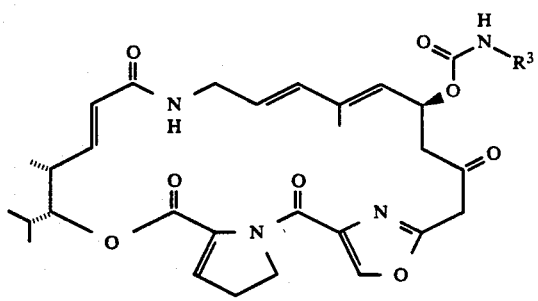

R$^3$ = Me
= o-NO$_2$C$_6$H$_4$
= m-NO$_2$C$_6$H$_4$
= p-NO$_2$C$_6$H$_4$
= C$_6$H$_5$
= m-tolyl
= naphth-1-yl Virginiamycin M$_1$ (0.50 g, 0.95 mmole) in anhydrous dichloromethane was added dropwise at room temperature to a solution of the respective isocyanate, R$^3$—N=C=O, (1.05 mmole) in dichloromethane (5 ml) and toluene (5 ml). Pyridine (85 μl) and dimethylaminopyridine (0.12 g) was added and the solution (except in the case of the methyl isocyanate solution) was refluxed (steam bath) for 30 minutes or until over 90% of starting material was consumed. Methanol (1 ml) was added and reflux continued for an additional 5 minutes. The reaction mixture was poured ove 50 ml saturated NaCl (aq) containing 0.5 ml conc. HCl and extracted with dichloromethane (3×50 ml). The organic layers were washed with saturated NaCl (aq), pooled, dried over anhydrous Na$_2$SO$_4$ and flash evaporated to dryness. Purification over a column of 50 g E. Merck silica gel 60 (43–60 μm particle size) using acetone/hexane or methanol/hexane/ethyl acetate mixtures yielded the desired carbanilates.

R$^3$=Me (Compound 7)
YIELD=0.074 g
HR FAB-MS(M$^+$): calculated for C$_{30}$H$_{38}$N$_4$O$_8$: 582.2689; found: 582.2528
(300 MHz)H$^1$-NMR(CD$_2$Cl$_2$), δ(ppm): 5.66(m), 2.69 (3H, d, J=5, CH$_3$)
(300 MHz)C$^{13}$-NMR(CD$_2$Cl$_2$), δ(ppm): 12.3, 12.9, 18.9, 19.7, 27.6, 30.2, 30.5, 38.0, 40.3, 45.6, 45.9, 51.1, 68.4, 81.6, 123.7, 125.5, 127.17, 127.24, 133.1, 136.2, 136.5, 137.1, 143.5, 145.6, 156.2, 156.4, 160.8, 161.2, 167.2, 199.5
FT-IR(ZnSe), ν(cm$^{-1}$): 3344, 2973, 1727, 1673, 1620
UV(MeOH), λ$_{max}$(nm, E %): 224 (sh, 468), 280 (sh, 146), 334 (69)
R$_f$=0.29 (E. Merck silica gel 60 F TLC plates (0.2 mm), Me$_2$CO: hexane, 50:50)

R$^3$=o—NO$_2$C$_6$H$_4$ (Compounds 8)
YIELD=0.024 g
HR FAB-MS(M+H$^+$): calculated for C$_{35}$H$_{39}$N$_5$O$_{10}$+H: 690.2775; found: 690.2849
(300 MHz)H$^1$-NMR(CD$_2$Cl$_2$), δ(ppm): 5.82(m), 7.40-8.38 (4H, m, aromatic)
(300 MHz)C$^{13}$-NMR(CD$_2$Cl$_2$), δ(ppm): 12.4, 13.0, 18.9, 19.7, 30.2, 30.6, 38.2, 40.2, 45.2, 46.0, 51.2, 70.0, 81.8, 121.0, 122.7, 123.8, 125.7, 126.1, 126.2, 127.9, 132.7, 135.6, 136.2, 136.4, 136.5, 137.2, 137.5, 143.4, 145.7, 152.2, 156.2, 160.8, 161.1, 167.2 199.1
FT-IR(ZnSe), ν(cm$^{-1}$): 3358, 2970, 1733, 1672, 1615
UV(MeOH), λ$_{max}$(nm, E %): 231 (666), 280 (sh, 192), 343 (58)
R$_f$=0.47 (E. Merck silica gel 60 F TLC plates (0.2 mm), Me$_2$CO: hexane, 50:50)

R$^3$=m—NO$_2$C$_6$H$_4$ (Compound 9)
YIELD=0.110 g
HR FAB-MS(M+H$^+$): calculated for C$_{35}$H$_{39}$N$_5$O$_{10}$+H: 690.2775; found: 690.2762
(300 MHz)H$^1$-NMR(CD$_2$Cl$_2$), δ(ppm): 5.82(m), 7.10-8.50 (4H, m, aromatic)
(300 MHz)C$^{13}$-NMR(CD$_2$Cl$_2$), δ(ppm): 12.5, 13.0, 19.0, 19.7, 30.3, 30.5, 37.9, 40.8, 45.7, 45.8, 51.0, 69.2, 81.4, 113.4, 117.7, 123.9, 124.5, 125.1, 126.4, 127.5, 130.0, 133.5, 136.2, 137.1, 137.2, 140.3, 144.2, 145.5, 149.0, 152.9, 156.6, 160.7, 161.4, 167.6, 199.3
FT-IR(ZnSe), ν(cm$^{-1}$): 3341, 2971, 1730, 1671, 1619
UV(MeOH), λ$_{max}$(nm, E %): 239 (698), 280 (sh, 199), 340 (36)
R$_f$=0.41 (E. Merck silica gel 60 F TLC plates (0.2 mm), Me$_2$CO: hexane, 50:50)

R$^3$=p-NO$_2$C$_6$H$_4$(Compound 10)
YIELD=0.200 g
HR FAB-MS(M+H$^+$): calculated for C$_{35}$H$_{39}$N$_5$O$_{10}$+H: 690.2775; found: 690.2775
(300 MHz)H$^1$-NMR(CD$_2$Cl$_2$), δ(ppm): 5.81(m), 7.58 (2H, d, J=9.5), 8.12 (2H, d, J=9.5), both aromatic
(300 MHz)C$^{13}$-NMR(CD$_2$Cl$_2$), δ(ppm): 12.5, 13.0, 18.9, 19.7, 30.3, 30.6, 38.0, 40.5, 45.4, 45.9, 51.1, 69.6, 81.6, 118.1, 118.1, 123.8, 125.3, 125.3, 125.4, 126.1, 127.7, 133.1, 136.3, 137.1, 137.3, 143.1, 143.9, 145.0, 145.7, 152.4, 156.4, 160.8, 161.4, 167.5, 199.1
FT-IR(ZnSe), ν(cm$^{-1}$): 3324, 2968, 1724, 1670, 1614,
UV(MeOH), λ$_{max}$(nm, %): 206 (263), 221 (279), 313 (114)
R$_f$=0.41 (E. Merck silica gel 60F TLC plates (0.2 mm), Me$_2$CO: hexane, 50:50)

R$^3$=C$_6$H$_5$ (Compound 11)
YIELD=0.082 g
HR FAB-MS(M+H$^+$): calculated for C$_{35}$H$_{40}$N$_4$O$_8$+H: 645.2924; found: 645.2942
(300 MHz)H$^1$-NMR(CD$_2$Cl$_2$), δ(ppm): 5.80(m), 7.00-7.40 (5H, m, aromatic)
(300 MHz)C$^{13}$-NMR(CD$_2$Cl$_2$), δ(ppm): 12.4, 13.0, 18.9, 19.7, 30.2, 30.5, 38.0, 40.4, 45.6, 45.9, 51.1, 68.8, 81.6, 118.9, 123.4, 123.7, 125.5, 126.8, 127.4, 129.2, 129.2, 133.2, 136.2, 136.8, 137.1, 138.6, 143.6, 145.6, 152.8, 156.4, 160.8, 161.3, 167.3, 199.4
FT-IR(ZnSe), ν(cm$^{-1}$): 3338, 2968, 1730, 1671, 1618
UV(MeOH), λ$_{max}$(nm, E %): 208 (sh, 371), 239 (666), 282 (sh, 147)
R$_f$=0.43 (E. Merck silica gel 60F TLC plates (0.2 mm), Me$_2$CO: hexane, 50:50)

R$^3$=m-tolyl (Compound 12)
YIELD=0.100 g
HR FAB-MS(M+Na$^+$): calculated for C$_{36}$H$_{42}$N$_4$O$_8$+Na: 681.2900; found: 681.2921
(300 MHz)H$^1$-NMR(CD$_2$Cl$_2$), δ(ppm): 5.78(m), 2.31 (3H, s, CH$_3$), 6.82-7.22 (4H, m, aromatic)
(300 MHz)C$^{13}$-NMR(CD$_2$Cl$_2$), δ(ppm): 12.4, 13.0, 18.9, 19.7, 21.5 (CH$_3$C$_6$H$_4$), 30.2, 30.6, 38.0, 40.4, 45.6, 45.9, 51.1, 68.8, 81.6, 116.0, 119.5, 123.7, 124.3, 125.5, 126.8, 127.4, 129.0, 133.2, 136.3, 136.9, 137.2, 138.4, 139.2, 143.6, 145.6, 152.7, 156.4, 160.8, 161.2, 167.3, 199.4
FT-IR(ZnSe), ν(cm$^{-1}$): 3358, 2976, 1732, 1671, 1617

UV(MeOH), λ$_{max}$(nm, E %): 212 (sh, 462), 240 (661), 284 (sh, 147)

R$_f$=0.46 (E. Merck silica gel 60F TLC plates (0.2 mm), Me$_2$CO: hexane, 50:50)

R$^3$=naphth-1-yl (Compound 13)

YIELD=0.098 g

HR FAB-MS(M+H+): calculated for C$_{36}$H$_{42}$N$_4$O$_8$+H: 695.3081; found: 695.3090

(300 MHz)H$^1$-NMR(CD$_2$Cl$_2$), δ(ppm): 5.85 (m), 7.42-7.88 (7H, m, aromatic)

(300 MHz)C$^{13}$-NMR(CD$_2$Cl$_2$), δ(ppm): 12.4, 13.0, 18.9, 19.7, 30.2, 30.5, 38.0, 40.4, 45.5, 45.9, 51.1, 69.3, 81.6, 119.7, 121.2, 123.7, 125.2, 125.5, 126.0, 126.3, 126.5, 126.7, 127.5, 128.8, 133.1, 134.4, 136.3, 137.1, 137.2, 143.5, 145.7, 153.6, 156.4, 160.8, 161.2, 167.3, 199.4

FT-IR(ZnSe), v(cm$^{-1}$): 3350, 2972, 1732, 1671, 1618

UV(MeOH), λ$_{max}$(nm, E %): 229 (634), 281 (210)

R$_f$=0.42 (E. Merck silica gel 60F TLC plates (0.2 mm), Me$_2$CO:hexane, 50:50)

EXAMPLE 14

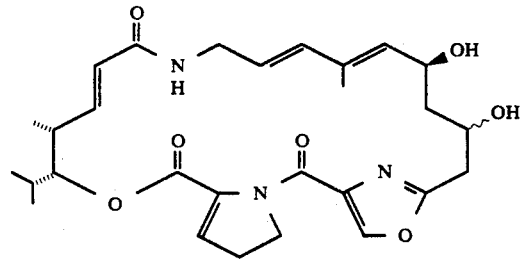

Sodium borohydride (325 mg, 8.59 mmole) in 40 ml methanolic solution was added in one shot to a stirred solution of Virginiamycin M$_1$ (3.84 g, 7.3 mmole) in methanol (150 ml) in an ice-water bath. Stirring continued for 15 minutes followed by addition of acetone (10 ml) to destroy excess reagent. Work-up involved flash evaporation of the reaction mixture to 65 ml and subsequent addition to ice-cold saturated NaCl (aq) (500 ml). Extraction with dichloromethane (5×250 ml), drying the organic layers over anhydrous Na$_2$SO$_4$, and flash evaporation to dryness below 35° C., gave 3.90 g of product. Flash chromatographic purification in a column of 200 g E. Merck silica 60 (43–60 μm particle size) using 10 to 20% i-propanol/dichloromethane mixtures for elution yielded 1.45 g of the more polar epimer and 1.75 g of the less polar epimer.

MORE POLAR EPIMER (14A)

HREI-MS(M+): calculated for C$_{28}$H$_{37}$N$_3$O$_7$: 527.2632; found: 527.2629

(300 MHz)H$^1$-NMR(CD$_2$Cl$_2$), δ(ppm): 4.63(m)

(300 MHz)C$^{13}$-NMR(CD$_2$Cl$_2$), δ(ppm): 12.3, 13.5, 19.0, 19.7, 30.2, 30.4, 37.1, 37.8, 40.8, 44.8, 51.4, 67.2, 67.7, 81.4, 124.6, 125.0, 125.4, 133.7, 134.4, 134.8, 135.7, 137.3, 144.1, 144.3, 161.1, 161.2, 162.1, 167.2

FT-IR(ZnSe), v(cm$^{-1}$): 3346, 2971, 1732, 1668, 1617

UV(MeOH), λ$_{max}$(nm, E %): 217 (sh, 539), 233 (571), 280 (sh, 142)

R$_f$=0.28 (E. Merck silica gel 60F TLC plates (0.2 mm), i-PrOH:CH$_2$Cl$_2$, 15:85)

LESS POLAR EPIMER (14B)

HREI-MS(M+): calculated for C$_{28}$H$_{37}$N$_3$O$_7$: 527.2632; found: 527.2623

(300 MHz)H$^1$-NMR(CD$_2$Cl$_2$), δ(ppm): 4.91(m)

(300 MHz)C$^{13}$-NMR(CD$_2$Cl$_2$), δ(ppm): 11.3, 13.0, 18.8, 19.7, 30.0, 30.4, 36.0, 37.5, 41.8, 42.5, 51.1, 66.8, 67.7, 80.9, 124.9, 124.9, 125.2, 133.4, 134.4, 136.1, 137.0, 137.4, 143.8, 144.2, 160.5, 161.2, 162.1, 167.0

FT-IR(ZnSe), v(cm$^{-1}$): 3339, 2973, 1733, 1668, 1619

UV(MeOH), λ$_{max}$(nm, E %): 218 (sh, 549), 235 (601), 280 (sh, 134)

R$_f$=0.45 (E. Merck silica gel 60F TLC plates (0.2 mm), i-PrOH:CH$_2$Cl$_2$, 15:85)

EXAMPLE 15

Radioligand binding assays

[$^{125}$I]BHCCK-8 binding to rat pancreatic and guinea pig cortical preparations were performed essentially as described by Lam, et al., *J. Antibiotics*, 44, 613–625 (1991). CCK-B and CCK-A selective antagonist ligand assays employing [$^3$H]L-365,260 and [$^3$H]L-364,718 respectively were performed essentially as described by Chang, et al., *Molecular Pharmacology*, 35, 803–808 (1989) and Chang, et al., *Molecular Pharmacology*, 30, 212–217 (1986) with the minor modifications noted below. For the [$^3$H]L-365,260 assay brain membranes were homogenized in 0.32M sucrose (20 vol) and centrifuged at 1000×g for 10 minutes. The resulting supernatant was re-spun at 20,000×g for 20 minutes. Pellets were resuspended at 1 g starting material to 60 ml of incubation buffer (20 mM HEPES, 1 mM EDTA, 150 mM NaCl and 0.25 mg/ml bacitracin, pH 7.4). Specific binding was defined with 1 μM CCK-8S using 1.5 nM radioligand. Incubations were for 40 minutes at 4° C. and were terminated by filtration and washing with ice cold 100 mM saline. For the [$^3$H]L-364,718 assay, pancreas was homogenized in 10 mM HEPES buffer, pH 7.4, containing 0.01% trypsin inhibitor. The final tissue resuspension was 1 g starting material to 2000 ml of assay buffer (20 mM HEPES, 1 mM EGTA, 5 mM MgCl$_2$, 150 mM NaCl, pH 7.4, containing 0.25 mg/ml bacitracin, 0.1 mg/ml trypsin inhibitor and 2 mg/ml bovine serum albumin). Incubations were for 30 minutes at room temperature and were terminated by filtration over GF/C filters and washing with 100 mM NaCl.

TABLE I

| CCK binding inhibition - IC$_{50}$ (M) | | | |
|---|---|---|---|
| CCK-B (guinea pig cortex) | | | |
| EX # | [$^{125}$I]BHCCK | [$^3$H]L-365,260 | A.R. |
| 1 | 0.8 | >3.0 (13%) | >25 |
| 2 | 0.7 | >3.0 (21%) | >25 |
| 3 | 0.6 | 1.0 | 2 |
| 4 | 0.5 | 1.2 | 2 |
| 5 | 0.6 | >3.0 (40%) | ~10 |
| 6 | 0.096 | 0.19 | 2 |
| 7 | 0.8 | >3.0 (14%) | 19 |
| 8 | 0.3 | 3.1 | 10 |
| 9 | 0.4 | 5.2 | 12.9 |
| 10 | 1.6 | 13.1 | 8.7 |
| 11 | 0.3 | 1.6 | 5.3 |
| 12 | 0.4 | 3.0 | 7.5 |
| 13 | 0.3 | 2.8 | 9.3 |
| 14A | 2.1 | 0.14 | 0.1 |
| 14B | 0.4 | 0.53 | 1 |
| CCK-A (rat pancreas) | | | |
| EX # | [$^{125}$I]BHCCK | [$^3$H]L-364,718 | A.R. |
| 1 | >3.0 (0%) | >3.0 (10%) | — |
| 2 | >3.0 (5%) | >3.0 (5%) | — |
| 3 | >3.0 (5%) | >3.0 (4%) | — |
| 4 | >3.0 (21%) | >3.0 (15%) | — |
| 5 | >3.0 (29%) | >3.0 (14%) | — |
| 6 | 2.3 | >3.0 (16%) | — |
| 7 | >3.0 (0%) | >3.0 (19%) | — |
| 8 | >3.0 (3%) | >3.0 (8%) | — |
| 9 | >3.0 (32%) | >3.0 (1%) | — |
| 10 | >3.0 (10%) | >3.0 (1%) | — |

TABLE I-continued

| | CCK binding inhibition - IC$_{50}$ (M) | | |
|---|---|---|---|
| 11 | 2.3 | 4 | 1.7 |
| 12 | 1.9 | 8.0 | 4.2 |
| 13 | 1.4 | 4.8 | 3.4 |
| 14A | >3.0 (5%) | >3.0 (15%) | — |
| 14B | >3.0 (1%) | >3.0 (5%) | — |

(A.R. = agonist ratio = IC$_{50}$ ([$^3$H]L-365,260)/IC$_{50}$ ([$^{125}$I]CCK))

EXAMPLE 16

Antimicrobial activity

Cultures employed in evaluating antimicrobial activity included plant pathogens, human and animal opportunistic pathogens and selected laboratory strains having specific-antibiotic sensitivities or chromosomal or R-plasmid-mediated resistances. Of the 21 Gram-positive and Gram-negative bacteria tested, the present compounds demonstrated antibotic activity only against Gran-positive organisms, with Mb 1101 being the most sensitive. The agar diffusion MIC's were determined using the method described by Barry in Anitbiotics in Laboratory Medicine, 2nd Ed., Ed. V. Lorian, pp. 1–63, William & Wilkins, Baltimore, 1986. Each test compound was dissolved in methanol to a concentration of 1 mg/ml. Serial dilutions of these compounds were also made to determine an agar diffusion MIC. 20 μl of each dilution was pipetted on to 6 mm paper discs, air dried and placed onto the surface of an agar plate seeded with the appropriate bacteria (~10$^6$ cfu). Seeded agar plates were incubated overnight (~18 hours) at 25° C. Zone sizes were measured to the nearest mm. Each compound was tested in triplicate and the results shown represent the mean.

TABLE II

Antibiotic Activity -
Inhibition zone diameters (mm) @ 20 g/disc

Gram Positive
Test organisms[a]

| | Baci | Sta | Subt | Micr | Sta | Cory | Str | Str |
|---|---|---|---|---|---|---|---|---|
| Merck No., Mb: | 633 | 108 | 964 | 1101 | 2983 | 261 | 2820 | 2875 |
| ATCC: | | | | | | | | |
| Ex # | — | 6538P | 6633 | 9341 | — | 9742 | — | — |
| 1 | 0 | 9 | 0 | 17[c] | 0 | 14[b] | 0 | 0 |
| 2 | 0 | 11 | 0 | 21 | 0 | 13[b] | 0 | 0 |
| 3 | 11 | 0 | 21 | 0 | 12[b] | 0 | 0 | 0 |
| 4 | 0 | 0 | 0 | 25 | 0 | 0 | 0 | 0 |
| 5 | 0 | 0 | 0 | 12 | 0 | 0 | 0 | 0 |
| 6 | 0 | 0 | 0 | 8 | 0 | 0 | 0 | 0 |
| 7 | 7[d] | 19 | 0 | 27 | 11 | 22 | 10 | 16 |
| 8 | 0 | 7 | 0 | 16 | 0 | 9 | 0 | 0 |
| 9 | 0 | 0 | 0 | 8 | 0 | 0 | 0 | 0 |
| 10 | 0 | 9 | 0 | 13 | 0 | 9 | 0 | 0 |
| 11 | 0 | 0 | 0 | 14 | 0 | 0 | 0 | 0 |
| 12 | 0 | 0 | 0 | 9 | 0 | 0 | 0 | 0 |
| 13 | 0 | 0 | 18 | 9 | 11[e] | 0 | 0 | 0 |
| 14A | 9[d] | 27 | 0 | 35 | 22 | 30 | 16 | 30 |
| 14B | 0 | 22 | 0 | 35 | 11 | 26 | 15[c] | 18 |

Gram Negative
Test organisms[a]

| | Salm | Coli | Pseu | Ent |
|---|---|---|---|---|
| Merck No., Mb: | 1287 | 1418 | 1231 | 835 |
| ATCC: | | | | |
| Ex # | — | — | 11607 | — |
| 1 | 0 | 0 | 0 | 0 |
| 2 | 0 | 0 | 0 | 0 |
| 3 | 0 | 0 | 0 | 0 |
| 4 | 0 | 0 | 0 | 0 |

TABLE II-continued

Antibiotic Activity -
Inhibition zone diameters (mm) @ 20 g/disc

| | | | | |
|---|---|---|---|---|
| 5 | 0 | 0 | 0 | 0 |
| 6 | 0 | 0 | 0 | 0 |
| 7 | 0 | 0 | 0 | 0 |
| 8 | 0 | 0 | 0 | 0 |
| 9 | 0 | 0 | 0 | 0 |
| 10 | 0 | 0 | 0 | 0 |
| 11 | 0 | 0 | 0 | 0 |
| 12 | 0 | 0 | 0 | 0 |
| 13 | 0 | 0 | 0 | 0 |
| 14A | 0 | 8[d] | 15[d] | 0 |
| 14B | 0 | 0 | 0 | 0 |

[a]Test organisms: Baci 633 = Bacillus sp.; Sta = Staphylococcus aureus; Subt 964 = Bacillus subtilis; Micr 1101 = Micrococcus luteus; Cory 261 = Corynebacterium pseudodiphtheriticum; Str 2820 = Streptococcus faecium; Str 2875 = Streptococcus agalactiae; Salm 1287 = Salmonella gallinarum; Coli 1418 = Escherichia coli; Pseu 1231 = Pseudomonas stutzeri; Ent 835 = En terobacter aergenes.
[b]Fuzzy zones.
[c]Slightly hazy zones.
[d]Hazy zones.
[e]Rings.

TABLE III

Antibacterial activity versus Micrococcus luteus

| | μg/disc | | | | | | | | Agar Diffusion MIC |
|---|---|---|---|---|---|---|---|---|---|
| Ex # | 1.25 | 2.50 | 5.00 | 10.0 | 20.0 | 40.0 | 80.0 | 160 | (μM) |
| 1 | NZ | NZ | 12 | 15 | 16 | NT | NT | NT | 1.92 |
| 2 | NZ | 7 | 14 | 18 | 21 | NT | NT | NT | 3.24 |
| 3 | NZ | 7 | 13 | 17 | 19 | NT | NT | NT | 2.51 |
| 4 | 12 | 16 | 19 | 21 | 22 | NT | NT | NT | 0.54 |
| 5 | NT | NT | 10 | 11 | 13 | 14 | 14 | NT | 0.41 |
| 6 | NT | NT | NT | 10 | 9 | 10 | 10 | 11 | 0.003 |
| 7 | 8 | 13 | 18 | 22 | 25 | NT | NT | NT | 1.74 |
| 8 | 12 | 15 | 15 | 16 | 16 | NT | NT | NT | 0.019 |
| 9 | NT | NT | NT | 8 | 9 | 10 | 11 | 11 | 0.82 |
| 10 | NZ | NZ | 7 | 10 | 12 | NT | NT | NT | 3.94 |
| 11 | 7 | 10 | 11 | 12 | 12 | NT | NT | NT | 0.05 |
| 12 | NT | NT | NT | NZ | NZ | NZ | NZ | NZ | >243 |
| 13 | NT | NT | NT | NZ | NZ | NZ | NZ | NZ | >230 |
| 14A | 25 | 27 | 29 | 31 | 33 | NT | NT | NT | 0.08 |
| 14B | 22 | 25 | 28 | 30 | 32 | NT | NT | NT | 0.24 |

[a]Mean of triplicate zone size (mm) after incubation @ 25° C. for ~18 hours.
NZ: No inhibition zone.
NT: Not tested.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:
1. A compound of formula I:

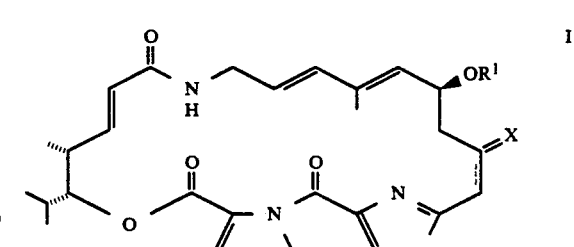

or a pharmaceutically acceptable salt thereof, wherein:
R$^1$ is selected from the group consisting of:
 (1) hydrogen
 (2) —COR$^2$, wherein R$^2$ is selected from the group consisting of:

(a) $C_{1-4}$ alkyl,
(b) benzyl, and
(c) phenyl, (3) —CONHR$^3$, wherein R$^3$ is selected from the group consisting of:
(a) $C_{1-4}$ alkyl,
(b) benzyl, unsubstituted or substituted with —CH$_3$ or —NO$_2$,
(c) phenyl, unsubstituted or substituted with —CH$_3$ or —NO$_2$,
(d) naphthyl, unsubstituted or substituted with —CH$_3$ or —NO$_2$, X is oxo, (H, OH) or (H, —OCOR$^4$), wherein R$^4$ is independently selected from the definitions of R$^2$, and the symbol of a line and a dashed line is a single bond or a double bond; with the proviso that if X is oxo or (H, OH), the symbol of a line and a dashed line is a single bond; and the further proviso that if X is oxo, R$^1$ is other than hydrogen.

2. The compound of claim 1 of the formula:

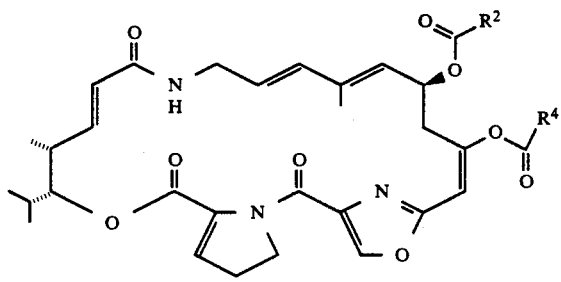

wherein R$^2$ and R$^4$ are independently selected from the group consisting of $C_{1-4}$alkyl, benzyl or phenyl.

3. The compound of claim 2 of the formula:

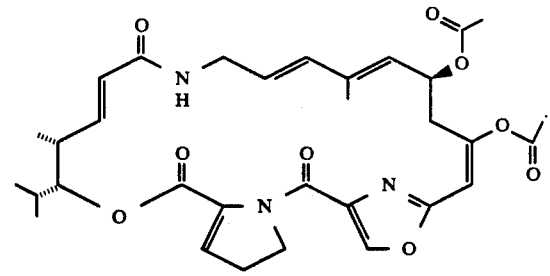

4. The compound of claim 1 of the formula:

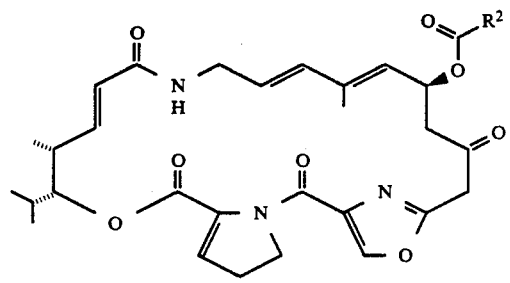

wherein R$^2$ is selected from the group consisting of $C_{1-4}$alkyl, benzyl or phenyl.

5. The compound of claim 4 which is selected from the group consisting of:

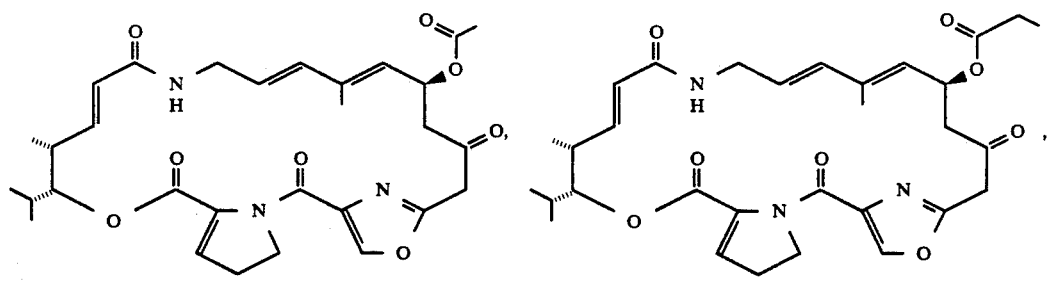

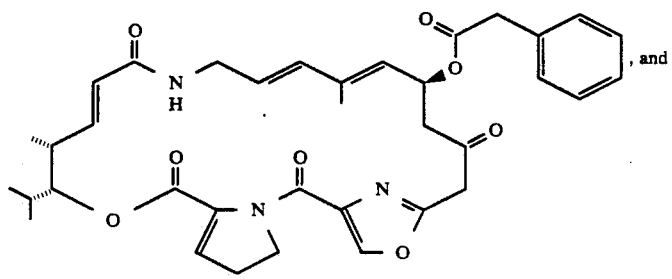

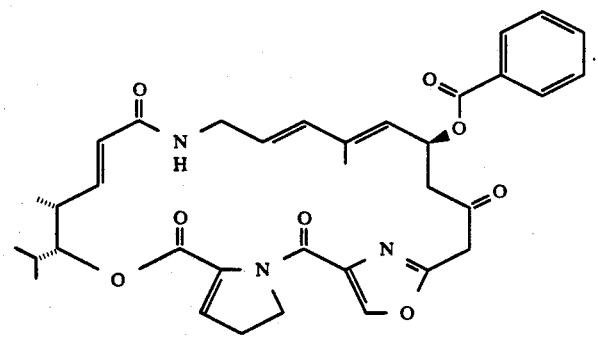

6. The compound of claim 1 of the formula:

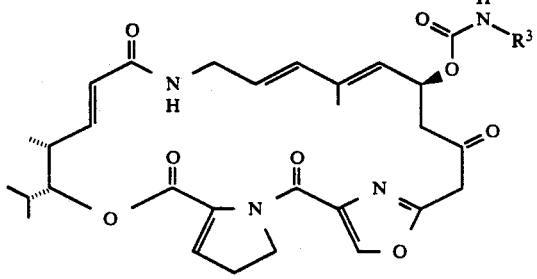

wherein R³ is selected from the group consisting of C₁₋₄alkyl, phenyl, benzyl or naphthyl, each optionally mono-substituted with methyl or —NO₂.

7. The compound of claim 6 wherein R³ is selected from the group consisting of methyl, ethyl, propyl, i-propyl, n-butyl, i-butyl, n-butyl, benzyl, phenyl, o-nitrophenyl, m-nitrophenyl, p-nitrophenyl, o-tolyl, m-tolyl, p-tolyl, naphth-1-yl or naphth-2-yl.

8. The compound of claim 7 wherein R³ is selected from the group consisting of methyl, phenyl, o-nitrophenyl, m-nitrophenyl, p-nitrophenyl, m-tolyl or naphth-1-yl.

9. The compound of claim 1 of the formula:

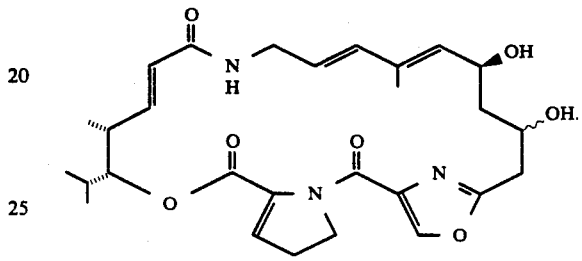

10. A pharmaceutical composition comprising a pharmaceutical carrier and a therapeutically effective amount of the compound of claim 1.

11. A method for the treatment of cholecystokinin or gastrin induced gastrointestinal disorders comprising the administration to a mammalian species in need of such treatment of an effective amount of the compound of claim 1.

12. A method for the treatment of central nervous system disorders comprising the administration to a mammalian species in need of such treatment of an effective amount of the compound of claim 1.

13. A method for regulating appetite comprising the administration to an animal in need of such regulating of an effective amount of the compound of claim 1.

14. A method for the promotion of growth comprising the administration to an animal in need of such promotion of an effective amount of the compound of claim 1.

15. A method for the treatment of bacterial infection comprising the administration to an animal of an effective amount of the compound of claim 1.

* * * * *